United States Patent
Milgramm et al.

(10) Patent No.: US 7,570,991 B2
(45) Date of Patent: Aug. 4, 2009

(54) METHOD FOR REAL TIME ATTITUDE ASSESSMENT

(75) Inventors: Michael Milgramm, Valley Stream, NY (US); Alex Imas, Niles, IL (US)

(73) Assignee: WaveSynch Technologies, Inc., Forest Hills, NY (US)

( * ) Notice: Subject to any disclaimer, the term of this patent is extended or adjusted under 35 U.S.C. 154(b) by 0 days.

(21) Appl. No.: 12/270,719

(22) Filed: Nov. 13, 2008

(65) Prior Publication Data

US 2009/0124922 A1   May 14, 2009

Related U.S. Application Data

(60) Provisional application No. 60/987,606, filed on Nov. 13, 2007.

(51) Int. Cl.
*A61B 5/00* (2006.01)
(52) U.S. Cl. ........................ 600/544; 600/300
(58) Field of Classification Search ........................ None
See application file for complete search history.

(56) References Cited

U.S. PATENT DOCUMENTS

| | | | |
|---|---|---|---|
| 5,243,517 A | | 9/1993 | Schmidt |
| 5,586,967 A | * | 12/1996 | Davis ........................ 600/28 |
| 6,021,346 A | * | 2/2000 | Ryu et al. ................... 600/544 |
| 6,067,467 A | | 5/2000 | John |
| 6,167,298 A | * | 12/2000 | Levin ........................ 600/545 |
| 6,434,419 B1 | | 8/2002 | Gevins |
| 6,609,024 B1 | | 8/2003 | Ryu et al. |
| 7,177,675 B2 | | 3/2007 | Suffin |
| 2001/0003145 A1 | * | 6/2001 | Mori et al. ................... 600/544 |
| 2005/0119547 A1 | | 6/2005 | Shastri et al. |
| 2005/0124848 A1 | * | 6/2005 | Holzner ........................ 600/9 |
| 2006/0036152 A1 | | 2/2006 | Kozel |
| 2006/0036153 A1 | | 2/2006 | Laken |
| 2008/0097235 A1 | | 4/2008 | Ofek et al. |

FOREIGN PATENT DOCUMENTS

| | | |
|---|---|---|
| WO | WO 2008/077175 | 7/2008 |
| WO | WO 2008/077176 | 7/2008 |
| WO | WO 2008/077177 | 7/2008 |
| WO | WO 2008/077178 | 7/2008 |
| WO | WO 2008/077179 | 7/2008 |

OTHER PUBLICATIONS

J. Peter Rosenfeld, "An EEG Biofeedback Protocol for Affective Disorders," Clinical Electroencephalography, Jan. 2000, 31(1), pp. 7-12.*

Muller, M.M., et al., Processing of affective pictures modulates right-hemispheric gamma band EEG activity, Clinical Neurophysiology, p. 110-111 (Nov. 1, 1999).

(Continued)

*Primary Examiner*—Robert L Nasser
(74) *Attorney, Agent, or Firm*—Gary J. Gershik; Cooper & Dunham LLP

(57) ABSTRACT

This invention provides an EEG-based method of determining whether a test subject possesses a sufficiently positive attitude to perform a predefined task with a second subject who is known to the test subject.

10 Claims, 6 Drawing Sheets

OTHER PUBLICATIONS

Meijer, Ewout H., et al., The P300 is sensitive to concealed face recognition, International Journal of Psychology, vol. 66, Issue 3, pp. 231-237 (Dec. 2007).

Simon-Thomas, Emiliana R., et al., Affective and cognitive modulation of performance monitoring: behavioral and ERP evidence, Cognitive, affective & behavioral neuroscience, p. 362-72 (Sep. 2005).

Aftanas, L.I., et al., Analysis of evoked EEG synchronization and desynchronization in conditions of emotional activation in humans: Temporal and topographic characteristics, Neuroscience and Behavioral Physiology, p. 859-867 (Aug. 1, 2004).

Hajcak G.; Olvet D.M., the Persistance of Attention to Emotion: Brain Potentials During and After Picture Presentation, Emotion, p. 250-255 (Apr. 1, 2008).

Herrmann, M.J. et al., Enhancement of activity of the primary visual cortex during processing of emotional stimuli as measured with event-related functional near-infrared spectroscopy and event-related potentials, Human Brain Mapping, p. 28-35 (Jan. 1, 2008).

Crites Jr., S., "Bioelectrical Echoes from Evaluative Categorization: II. A late Positive Brain Potential That Varies as a Function of Attitude Registration Rather Than Attitude Report", J. Personality and Social Psychology, 68(6):997-1013.

International Search Report issued Jan. 16, 2009 in connection with the counterpart PCT International Application No. PCT/US2008/012812.

Written Opinion issued Jan. 16, 2009 in connection with the counterpart PCT International Application No. PCT/US2008/012812.

* cited by examiner

METHOD FOR REAL TIME ATTITUDE ASSESSMENT

This application claims benefit of U.S. Provisional Application No. 60/987,606, filed Nov. 13, 2007, the contents of which are hereby incorporated by reference.

BACKGROUND OF THE INVENTION

It is a commonly known fact that when one places two conducting electrodes connected to a voltmeter, one on the scalp and the other on an electrically neutral area, such as the mastoids behind the ears, a quantifiable voltage can be observed. This voltage signal and its change with respect to time is the basis of electroencephalography, or EEG. The signal measured on the scalp is actually a summation of individual postsynaptic potentials occurring within the brain. Since both the neural tissue and the skull act as a low pass filter, it is unlikely that the high frequency transients of action potentials would make it up to the scalp, and since postsynaptic potentials generally have lower frequency transients associated with them, it is widely believed that the observed EEG signal originates from them.

The EEG recording is characterized by amplitude, frequency and their change over time. The frequency component of the EEG can be utilized to infer the level of an individual's neural activity. The frequencies are broken down into ranges which describe how alert and conscious a person is at any given time. The delta frequency (1-4 Hz) is associated with deep sleep. The theta frequency (5-7 Hz) is associated with drowsiness, and delta activity is also common. The alpha frequency (8-13 Hz) is associated with relaxed wakefulness, where not much brain resources are devoted to any one thing. The beta frequency (12-20 Hz, or 30 Hz) and the gamma frequency (36-44 Hz) are associated with alert attentiveness.

The technology disclosed herein, which uses EEG analysis, can be used to screen an individual so that a particular croup may be created in the most efficient manner possible based on a real time attitude assessment of the individual.

SUMMARY OF THE INVENTION

A method of determining whether a test subject possesses a sufficiently positive attitude to perform a predefined task with a second subject who is known to the test subject comprising:

a. determining from a first electroencephalograph (EEG) of the test subject recorded over a first period of time if the subject is alert enough to proceed to step b) of the method, and if so, proceeding to step b);

b. recording a second EEG over a second period of time from the test subject wherein the second EEG is recorded using a bilateral electrode with one pole of the bilateral electrode positioned over the left cerebral hemisphere (LCH) of the test subjects' brain and with another pole of the bilateral electrode positioned over the right cerebral hemisphere (RCH) of the test subjects' brain;

c. exposing the specific individual during the second period of time to a first series of visual images, the first series comprising at least one image of the face of the second subject and at least four images not of the face of the second subject, and quantitating (a) the amplitude of a P300 waveform evoked by the image of the face of the second subject and (b) the level of alpha and beta wave activity in the test subject during the second period of time;

d. determining from the amplitude of the P300 waveform if the second subject is known to the test subject;

e. recording a third EEG over a third period of time from the test subject;

f. exposing the test subject during the third period of time to a second series of visual images which images are predetermined not to evoke a P300 response in a population of test subjects and quantitating the level of alpha and beta wave activity in the test subject during the third period of time so as to determine baseline line alpha and beta wave activity;

g. subtracting the baseline alpha and beta wave activity quantitated in step f) from the alpha and beta wave activity, respectively, quantitated in step c) so as to produce corrected alpha and beta activity levels;

h. determining the ratio of corrected alpha wave activity to corrected beta wave activity, i. determining if the ratio of corrected alpha wave activity to corrected beta wave activity is higher in the LCH of the test subject or the RCH of the test subject, wherein a higher alpha/beta ratio in the LCH indicates that the test subject has a sufficiently positive attitude to perform the predefined task with the second subject, and wherein a higher alpha/beta ratio in the RCH indicates that the test subject does not have a sufficiently positive attitude to perform the predefined task with the second subject.

A method for determining whether a test subject determine if a subject has a mental state in regard to a second subject that is either 1) excited and/or happy; 2) content and/or calm; 3) sad and/or depressed; or 4) angry and/or afraid, the method comprising:

a. determining from a first electroencephalograph (EEG) of the test subject recorded over a first period of time if the subject is alert enough to proceed to step b) of the method, and if so, proceeding to step b);

b. recording a second EEG over a second period of time from the test subject wherein the second EEG is recorded using a bilateral electrode with one pole of the bilateral electrode positioned over the left cerebral hemisphere (LCH) of the test subjects' brain and with another pole of the bilateral electrode positioned over the right cerebral hemisphere (RCH) of the test subjects' brain;

c. exposing the specific individual during the second period of time to a first series of visual images, the first series comprising at least one image of the face of the second subject and at least four images not of the face of the second subject, and quantitating (a) the amplitude of a P300 waveform evoked by the image of the face of the second subject and (b) the level of alpha and beta wave activity in the test subject during the second period of time;

d. determining from the amplitude of the P300 waveform if the second subject is known to the test subject;

e. recording a third EEG over a third period of time from the test subject;

f. exposing the test subject during the third period of time to a second series of visual images which images are predetermined not to evoke a P300 response in a population of test subjects and quantitating the level of alpha and beta wave activity in the test subject during the third period of time so as to determine baseline line alpha and beta wave activity;

g. subtracting the baseline alpha and beta wave activity quantitated in step f) from the alpha and beta wave activity, respectively, quantitated in step c) so as to produce corrected alpha and beta activity levels;

h. determining the ratio of corrected alpha wave activity to corrected beta wave activity, i. determining if the ratio of corrected alpha wave activity to corrected beta wave activity is higher in the LCH of the test subject or the RCH of the test subject, wherein (1) a higher alpha/beta ratio in the RCH than LCH and an alpha/beta ratio in excess of two standard deviations indicates that the subject is content and/or calm; (2) a higher alpha/beta ratio in the LCH than RCH and an alpha/beta ratio in excess of two standard deviations indicates that the subject is sad and/or depressed; (3) a higher alpha/beta ratio in the RCH than LCH and an alpha/beta ratio below two standard deviations indicates that the subject is excited and/or happy; and (4) a higher alpha/beta ratio in the LCH than RCH and an alpha/beta ratio below two standard deviations indicates that the subject is angry and/or afraid.

DETAILED DESCRIPTION OF THE INVENTION

Figure 1:
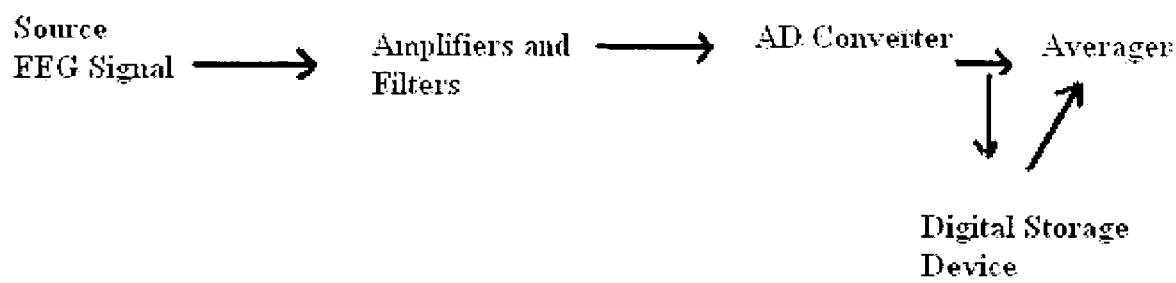
FIG. 1: Process for collecting EEG information.

A method of determining whether a test subject possesses a sufficiently positive attitude to perform a predefined task with a second subject who is known to the test subject comprising:

a. determining from a first electroencephalograph (EEG) of the test subject recorded over a first period of time if the subject is alert enough to proceed to step b) of the method, and if so, proceeding to step b);

b. recording a second EEG over a second period of time from the test subject wherein the second EEG is recorded using a bilateral electrode with one pole of the bilateral electrode positioned over the left cerebral hemisphere (LCH) of the test subjects' brain and with another pole of the bilateral electrode positioned over the right cerebral hemisphere (RCH) of the test subjects' brain;

c. exposing the specific individual during the second period of time to a first series of visual images, the first series comprising at least one image of the face of the second subject and at least four images not of the face of the second subject, and quantitating (a) the amplitude of a P300 waveform evoked by the image of the face of the second subject and (b) the level of alpha and beta wave activity in the test subject during the second period of time;

d. determining from the amplitude of the P300 waveform if the second subject is known to the test subject;

e. recording a third EEG over a third period of time from the test subject;

f. exposing the test subject during the third period of time to a second series of visual images which images are predetermined not to evoke a P300 response in a population of test subjects and quantitating the level of alpha and beta wave activity in the test subject during the third period of time so as to determine baseline line alpha and beta wave activity;

g. subtracting the baseline alpha and beta wave activity quantitated in step f) from the alpha and beta wave activity, respectively, quantitated in step c) so as to produce corrected alpha and beta activity levels;

h. determining the ratio of corrected alpha wave activity to corrected beta wave activity, i. determining if the ratio of corrected alpha wave activity to corrected beta wave activity is higher in the LCH of the test subject or the RCH of the test subject, wherein a higher alpha/beta ratio in the LCH indicates that the test subject has a sufficiently positive attitude to perform the predefined task with the second subject, and wherein a higher alpha/beta ratio in the RCH indicates that the test subject does not have a sufficiently positive attitude to perform the predefined task with the second subject.

A method for determining whether a test subject determine if a subject has a mental state in regard to a second subject that is either 1) excited and/or happy; 2) content and/or calm; 3) sad and/or depressed; or 4) angry and/or afraid, the method comprising:

a. determining from a first electroencephalograph (EEG) of the test subject recorded over a first period of time if the subject is alert enough to proceed to step b) of the method, and if so, proceeding to step b);

b. recording a second EEG over a second period of time from the test subject wherein the second EEG is recorded using a bilateral electrode with one pole of the bilateral electrode positioned over the left cerebral hemispheres (LCH) of the test subjects' brain and with another pole of the bilateral electrode positioned over the right cerebral hemisphere (RCH) of the test subjects' brain;

c. exposing the specific individual during the second period of time to a first series of visual images, the first series comprising at least one image of the face of the second subject and at least four images not of the face of the second subject, and quantitating (a) the amplitude of a P300 waveform evoked by the image of the face of the second subject and (b) the level of alpha and beta wave activity in the test subject during the second period of time;

d. determining from the amplitude of the P300 waveform if the second subject is known to the test subject;

e. recording a third LEG over a third period of time from the test subject;

f. exposing the test subject during the third period of time to a second series of visual images which images are predetermined not to evoke a P300 response in a population of test subjects and quantitating the level of alpha and beta wave activity in the test subject during the third period of time so as to determine baseline line alpha and beta wave activity;

g. subtracting the baseline alpha and beta wave activity quantitated in step f) from the alpha and beta wave activity, respectively, quantitated in step c) so as to produce corrected alpha and beta activity levels;

h. determining the ratio of corrected alpha wave activity to corrected beta wave activity, i. determining if the ratio of corrected alpha wave activity to corrected beta wave activity is higher in the LCH of the test subject or the RCH of the test subject, wherein (1) a higher alpha/beta ratio in the RCH than LCH and an alpha/beta ratio in excess of two standard deviations indicates that the subject is content and/or calm; (2) a higher alpha/beta ratio in the LCH than RCH and an alpha/beta ratio in excess of two standard deviations indicates that the subject is sad and/or depressed; (3) a higher alpha/beta ratio in the RCH than LCH and an alpha/beta ratio below two standard deviations indicates that the subject is excited and/or happy; and (4) a higher alpha/beta ratio in the LCH than RCH and an alpha/beta ratio below two standard deviations indicates that the subject is angry and/or afraid.

In an embodiment in step a) the test subject is determined to be alert by:

recording an electroencephalograph (EEG) over a period of time from the test subject using an EEG recording apparatus;

analyzing the frequency distribution of the wavebands recorded in the EEG; and quantitating any ERN (error related negativity) waveform in the EEG, wherein presence in the EEG of both (1) (a) an alpha waveband power component ratio of 0.5-1.0 and a theta waveband power component ratio of less than 0.5 or (b) a theta waveband power ratio of 0.5-1.0 and an alpha waveband power component ratio of less than 0.5; and (2) one or more ERN waveforms recorded during the period of time indicates that the test subject is not sufficiently alert to perform the predefined task, and wherein the presence of (1) but not (2), or (2) but not (1), indicates that the test subject is sufficiently alert to perform a predefined task, In an embodiment steps e) and f) can be performed before steps b) and c).

In an embodiment at least one of the EEGs is recorded using electrodes each comprising an Ag—AgCl recording tip. In an embodiment one electrode records from a Pz site on the test subject's head. In an embodiment the EEG is recorded using at least four electrodes, with three recording from the Pz site on the test subject's head and one recording from a mastoid area of the test subject's head. In an embodiment the methods further comprise correcting the first, second and/or third EEG for test subject's eye blinks. In an embodiment the EEG is corrected for test subject's eye blinks as measured by a fiber-optic eye blink detector. In an embodiment a 3-D reconstruction of the EEG recorded is not performed.

In an embodiment, the test subject is not presented with a target stimulus.

In regard to determining the ratio of corrected alpha wave activity to corrected beta wave activity, the baseline beta and alpha readings form a normal population for each individual. The normal population has a certain mean x (which is different for each individual) and a standard deviation value s.d. (which is also different for each individual). Alpha and beta readings will be recorded when the respective images are shown on the screen. These values and ratios are statistically compared to the baseline values and if they fall 2 s.d. values away from the baseline mean then they are considered different to a statistically significant degree.

An "increase" or "decrease" in alpha/beta activity refers to a statistically significant difference wherein the new value falls 2 standard deviations to the right or left of the baseline mean.

In regard to the power component ratio, a frequency band power is computed through a Power Spectrum Analysis (PSA) wherein a Fast Fourier Transform (FFT) is applied to the raw EEG signal and a power spectrum is computed ($\mu V^2$/Hz). The spectrum is then condensed and analyzed into frequency bands divided into delta (1-4 Hz), theta (4-8 Hz), alpha (8-12 Hz) and beta (12-20 Hz) components. Power component ratios are then determined by dividing the power of the particular frequency band by the sum of the powers of all of the recited frequency bands. Thus an alpha power component ratio would be: Alpha power/(delta power+theta power+alpha power+beta power).

Where a range is give it is understood that the range includes all integers and 0.1 units within that range, and any sub-range thereof. For example, a range of 30 minutes to 24 hours includes the times 31 minutes, 32 minutes etc., as well as the ranges 45 minutes to 55 minutes, 44 minutes to 59 minutes, etc.

In embodiments the alpha waveband power component ratio is 0.5, 0.55, 0.6, 0.65, 0.7, 0.75, 0.8, 0.85, 0.9, 0.95, or 1.0, or any range thereof, when the theta waveband power component ratio is less than 0.5.

In embodiments the theta waveband power component ratio is 0.5, 0.55, 0.6, 0.65, 0.7, 0.75, 0.8, 0.85, 0.9, 0.95, or 1.0, or any range thereof, when the alpha waveband power component ratio is less than 0.5.

Every embodiment described herein may be performed employing a computer and associated relevant apparatus as described herein.

All combinations of the various elements described herein are within the scope of the invention.

Experimental Details

EEG recording and the apparatus that may be used therefor are described in Allison et al., U.S. Patent Application Publication No. 2005/0017870; Preston, U.S. Pat. No. 5,267,570; Gevins, U.S. Pat. No. 5,724,987; Gevins, U.S. Pat. No. 5,447,166; Gevins, U.S. Pat. No. 5,295,491; Maynard, U.S. Pat. No. 5,816,247; Burton, U.S. Patent Application Publication No. 2004/0044293; Levendowski et al., U.S. Pat. No. 6,625,485; Levendowski et al., U.S. Pat. No. 6,496,724; Johnson, U.S. Pat. No. 6,754,524; Moore-Ede, U.S. Pat. No. 6,511,424; Moore-Ede, U.S. Pat. No. 6,070,098; and Pavelka., WO 2006/000166, each of which is hereby incorporated by reference.

Attitude Assessment and EEG Based Qualification of Emotion

Physiology

Neurologically, the limbic system, which is also involved in motivation and memory processing, is responsible for the initial emotional interpretation of a given stimulus. The processed signal is then sent to the hypothalamus which analyzes it further and triggers an appropriate physical response (increased heart rate for fear, sweating for anxiety, etc). The signal then travels to the amygdala where it is associated with a template of emotional reactions such as reward or fear, and compared to previous experiences before going on to further processing in the cortex. Since the limbic system is located within the brain, the progression just described cannot be detected through electrical means on the scalp.

After the limbic system, the signal travels to the temporal and prefrontal cortices where the visceral sensations described herein are processed on a cognitive level. The prefrontal lobe acts as an emotional control center, and since it is part of the outer cortex, its activity can be measured from the scalp.

Distinguishing Emotions

Emotional assessments are made through the use of alpha/beta frequency ratios. Alpha waves typically fall in the 8-12

Figure 6:
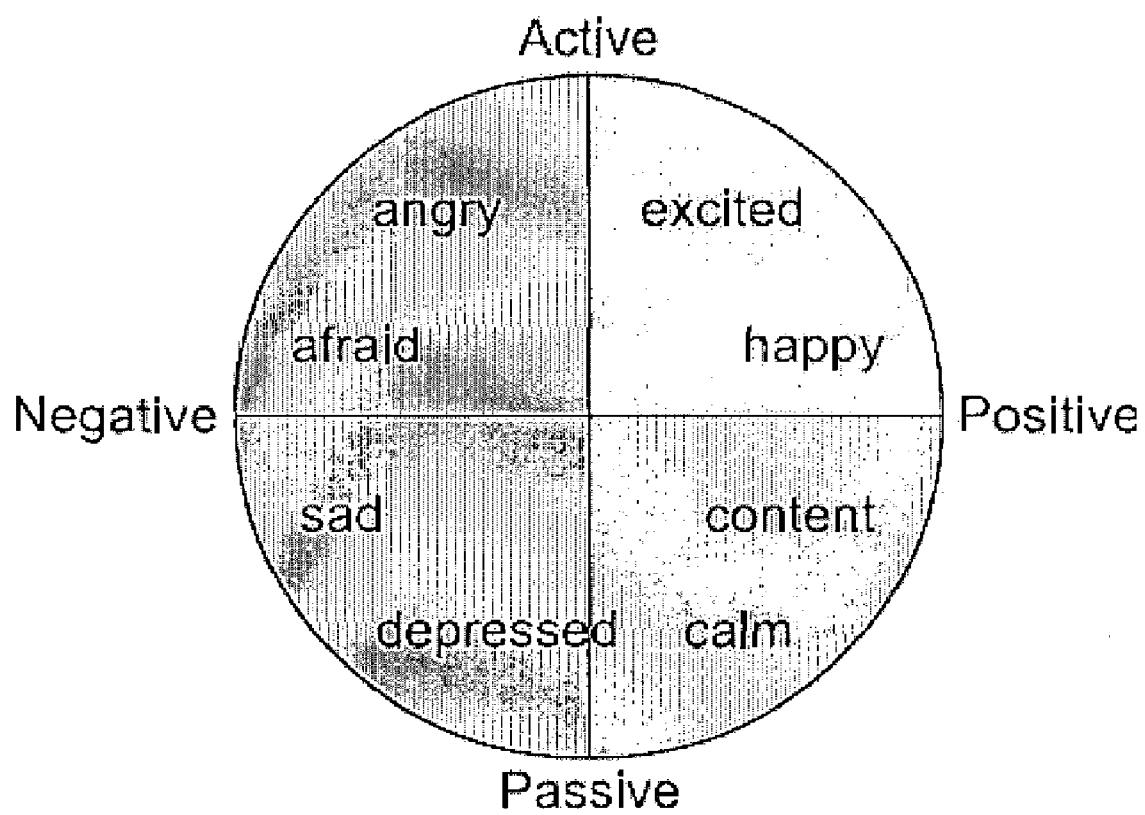
FIG. 6: Emotional quadrants schematic.

Hz range and indicate a state of lower brain activity and relaxation. Beta waves fall typically within the 12-30 Hz range and indicate a state of heightened brain activity. In terms of discriminating between emotional responses, Lang's model of valence and arousal is typically used. Valence measures the nature of the emotion, whether it is positive/approach or negative/withdrawal, and arousal measures the intensity of the emotion, calm versus excited. The emotional field is divided into four quadrants as shown in FIG. 6.

When distinguishing where a particular emotional response should be placed, alpha and beta frequencies are analyzed. The larger the proportion of alpha to beta waves, the less aroused the emotional response. Hence, a high alpha/beta ratio would place the emotional response in the lower two quadrants. Left prefrontal lobe inactivation is a sign of a negative/withdrawal response while right prefrontal lobe inactivation is a sign of a positive/approach response. Hence if a bilateral electrode was set up over the two hemispheres of the brain, a higher alpha/beta ratio over the left lobe would indicate a negative emotional response while a higher alpha/beta ratio over the right lobe would indicate a positive emotional response. These measurements determine the valence, and taken together with arousal, would place the emotional response into one of the four quadrants. One issue with this approach is that these readings do not so much qualify affective valence (the feeling of a particular emotion), but a motivational direction, namely whether the subject wants to approach or withdraw from the stimulus. For the most part, this method will generate results that correspond to affective valence. Care must be taken with the emotion of anger. Anger would indicate a low alpha/beta ratio, meaning high brain activity, but would also indicate a higher alpha/beta ration over the right lobe rather than the left since the person wants to approach and remove the stimulus rather than withdraw from it.

The subject's EEG recordings will first be analyzed to produce a general frequency band layout. Principle component analysis (PCA) will be used to calculate each ratio addressed in this document. An alpha/beta frequency ratio will be calculated in order to determine whether the subject is alert enough for the test. A ratio above a certain threshold would mean that the subject is not alert and he or she will have to come back for testing at a later time. If the subject passes the test, they will then be presented with an image of the stimulus in question (image of a workplace factor) intermixed with a set of irrelevant stimuli, and a P300 response will be measured to indicate that the subject does indeed recognize the stimulus and is familiar with it.

Next, two emotionally neutral images will be displayed. The images will be taken from the emotion annotated image library (IAPS), a database of visual images whose emotional responses have already been determined over an extensive population study. These neutral images will act as the baseline frequencies for both alpha and beta frequency bands. The stimulus of interest will then be displayed and the subject's brain activity recorded. The baseline will be subtracted from the recorded frequency bands and the alpha/beta ratios calculated accordingly. The method for classifying emotion described above will then be applied.

These three steps will determine the subject's attitude towards a given stimulus. The first two steps act as controls to make sure that the subject being tested is in a proper mental state (attentive, self aware), and the third step will determine in what way the subject regards the stimulus in question.

EEG recording and the apparatus used therefor are described in Allison et al., U.S. Patent Application Publication No. 2005/0017870; Preston, U.S. Pat. No. 5,267,570; Gevins, U.S. Pat. No. 5,724,987; Gevins, U.S. Pat. No. 5,447,166; Gevins, U.S. Pat. No. 5,295,491; Maynard, U.S. Pat. No. 5,816,247; Burton, U.S. Patent Application Publication No. 2004/0044293; Levendowski et al., U.S. Pat. No. 6,625,485; Levendowski et al., U.S. Pat. No. 6,496,724; Johnson, U.S. Pat. No. 6,754,524; Moore-Ede, U.S. Pat. No. 6,511,424; Moore-Ede, U.S. Pat. No. 6,070,098; and Pavelka., WO 2006/000166, each of which is hereby incorporated by reference.

Traditionally, an EEG was recorded using hollow disk electrodes made from tin, silver or gold. The electrodes were attached to the subject's scalp using conduction paste in order to minimize noise and impedance of the signal. The subject's scalp had to be prepared by cleansing the areas involved in the experiment usually through abrasion. Recently, a new type of electrode has been developed that functions through an active setup. The electrode is able to tolerate high levels of impedance and consequently prior skin preparation is no longer necessary. The new electrode, available as for example the BioSemi Pin-Type active electrode, contains an Ag—AgCl tip which eliminates most noise and significantly lowers signal impedance. The electrode is fitted into specially designed holders on the BioSemi headcap which are filled with electrode gel through a syringe. The elastic headcap is then fitted atop the subjects head and the EEG data collection can begin. The technology disclosed herein can employ the active electrode setup so as to minimize time and participant discomfort. After the electrode holders are filled with gel and the appropriate electrodes are attached, the electroencephalogram of many individuals can be obtained without any further setup. The individual in charge of running the biometric technology replaces the electrode gel as needed.

In order to record EEG, a minimum of two electrodes is necessary. One electrode must be placed at the reference point and another at the site of interest. The reference point should be electrically neutral so as to act as a baseline (different from the pre-signal baseline used to measure ERPs) which coupled with the signal from the electrode on the scalp will be used to calculate the EEG voltage potential readings. Typically the mastoids or the ears are used as the reference point: the mastoids being well insulated by a particularly thick layer of bone to impede the signal and the ears being far enough from the signal source to pick up anything substantial. In the present case bilateral electrodes are used so as to differentiate between left cerebral hemisphere and right cerebral hemisphere activity.

The EEG signal can be distorted by external noise signals which have a variety of sources. The source of noise that would most significantly affect the technology is blinking. When an individual blinks it causes a significant jump in the voltage potential that may be interpreted as an event related potential. Several techniques have been developed to eliminate the influence of this artifact. Many practitioners apply two additional electrodes for electrooculography (EOG) recording diagonally above and below the eye to pick up vertical and horizontal eye movements. When the voltage potential from those two electrodes exceeds a certain threshold, over 80 µV in most protocols, that particular trial is disregarded as containing an artifact so that only error-free trials are kept. This is accomplished through a program, introduced by Gratton, Coles and Donchin in 1983 and further developed by Ziegler and Gattaz in 1992, which determines the magnitude of correlation between eye electrodes' vertical and horizontal leads and the EEG signal. For the purposes of the technology described here, the number of electrodes necessary for EEG recording can be minimized by an eye sensor that detects blinks, such as the Fiber-Optic Eye-Blink Switch (PSSW-EB), that is used to detect blinks and then signal for the EEG recording program to eliminate those trials. This will eliminate the need for EOG recording.

FIG. 1 describes the path of the raw EEG signal as it is converted into a form that is usable for analytical purposes. The signal is first passed through amplifying and filtering systems which increase the strength of the signal, accentuate the desired portions and filter out any unwanted frequencies. The gain should be set high enough so that the amplitude is sufficiently sensitive to pick up small deflections, but low enough so that saturation or clipping does not occur. The filtering system should couple a low pass and high pass filter in order to control for noise or artifacts. A typical protocol for recording P300 ERPs sets the low pass filter at 30 Hz and the high pass filter at 0.3 Hz (Rosenfeld et al 2003). The modified signal is then sent to an Analog to Digital Converter (A/D Converter) which samples the analog signal, typically at 100 Hz, and converts the data into a digital stream. The EEG recording is now usable for software analysis. Applying a Fast Fourier Transform (FFT) at this point decomposes the complex signal into its underlying sine wave constituents, and a frequency band diagram can be composed that illustrates the prominence of different frequencies in the subject's EEG recording.

An electroencephalogram can be decomposed into frequency bands which can then be analyzed to determine the person's attentive state using power ratio component analysis for example.

Event Related Potential:

For the purposes of the technology disclosed here a particular component of the EEG can be analyzed called the Event Related Potential (ERP). Essentially, the ERP is the body's psychophysiological response to a given stimulus. Since individual neurons have relatively little electrical activity associated with them, certainly not enough to be detected on the scalp, ERPs are recorded when neurons act synchronously and the electric fields generated by each particular neuron are oriented in such a way that the effects on the scalp cumulate. Only neurons organized in a layered open field manner (neurons with dendrites and axons oriented in the same fashion) are picked up as an ERP. Given that property, an infinite amount of generators in different parts of the brain can be producing the ERP; just because an ERP is detected in a certain place on the scalp does not mean that it is being generated from a single area within the brain—you can infer location of surface activity but not internal activity. Stimuli that cause ERPs can either be external, such as the memory coupled stimulus that invoices the P300, or internal, such as the rhythmic pacemaker-like oscillations projected by the nucleus reticularis to thalamic nuclei and the cortex.

Figure 2:
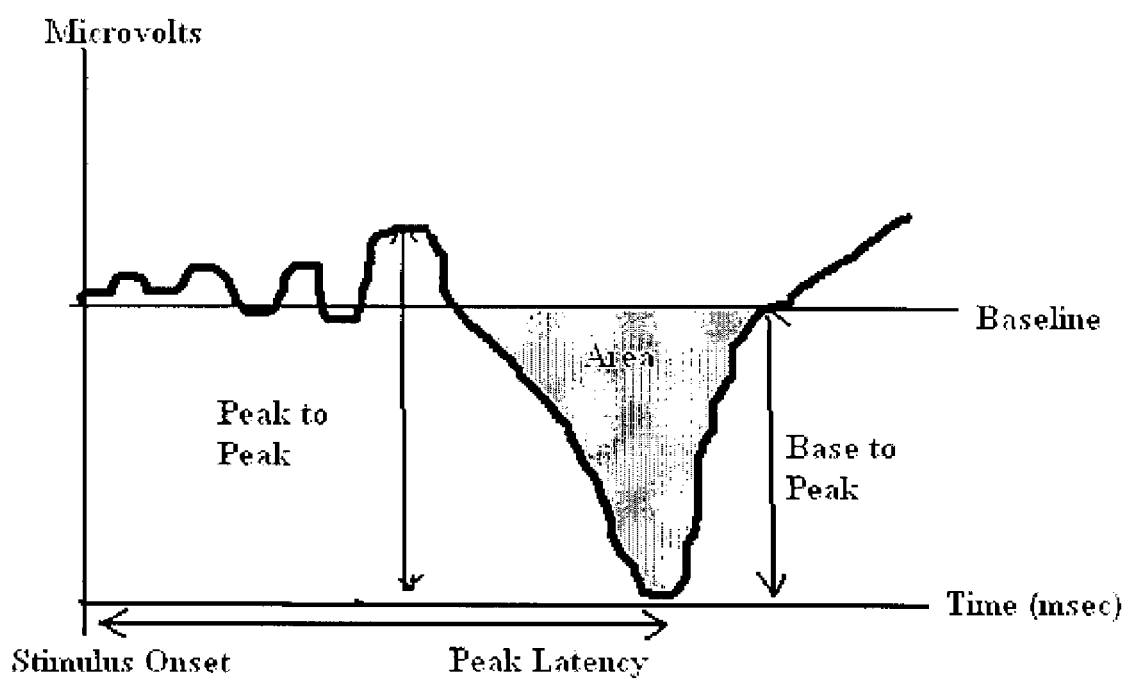
FIG. 2: An Event Related Potential—the P300 waveform

ERPs are generally small, about 50 $\mu V$, in comparison to the overall EEG recording. Hence, in order to perform an analysis on it the discrimination of the signal must be increased from the background noise of the general EEG. In order to accomplish this, the EEG recording is sent to the Averager. In order to average out the EEG noise, the ERP signal must be constant over trials, the noise must be random across trials and the ERP signal must be independent of background noise. Therefore, because the ERP signal is time locked, the EEG background noise can be averaged out leaving only the desired ERP signal. The number of samples used in the average is related to the signal to noise ratio, so a minimum of 20 samples must be used to produce a viable ERP. The result is a voltage vs. time function containing a number of positive and negative peaks. ERPs are described in terms of their characteristic scalp distribution, polarity and latency; a typical ERP readout (in this case the P300) is pictured in FIG. 2.

Figure 3:
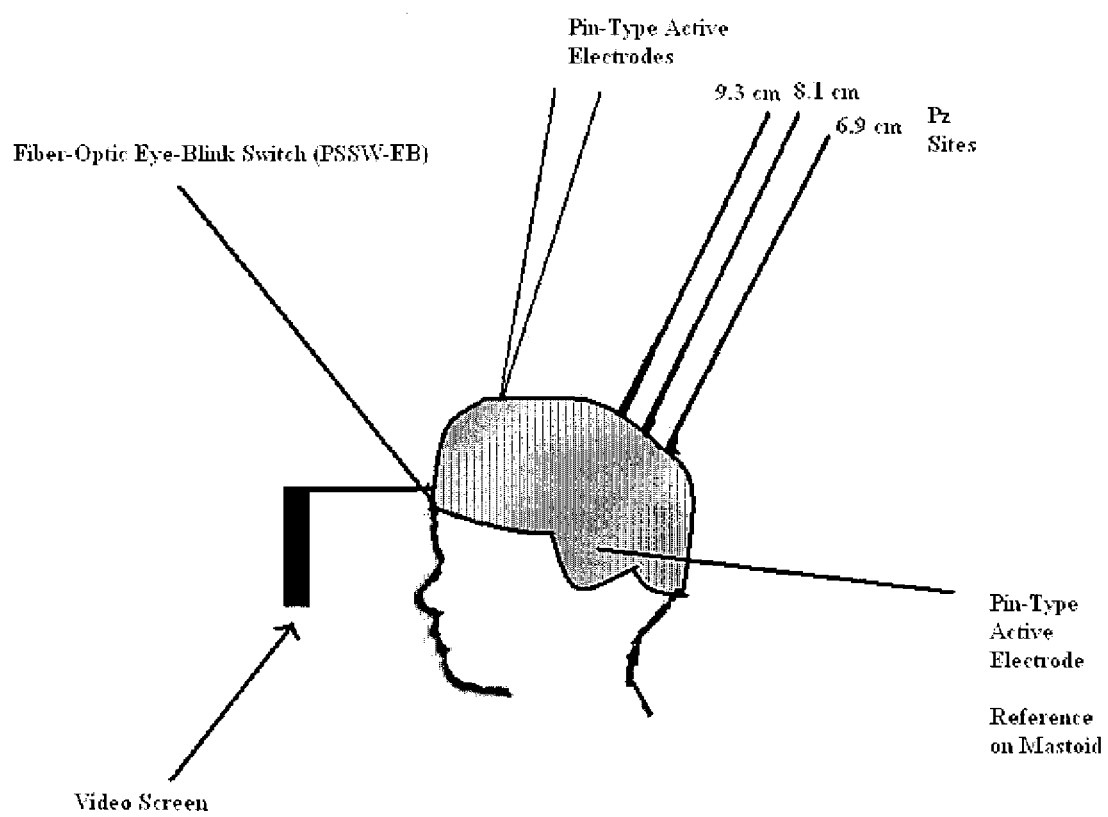
FIG. 3: Pin electrode EEG headcap device (with fiber optic blink switch), including an optional screen (e.g. video) for presenting visual images.
Figure 4:
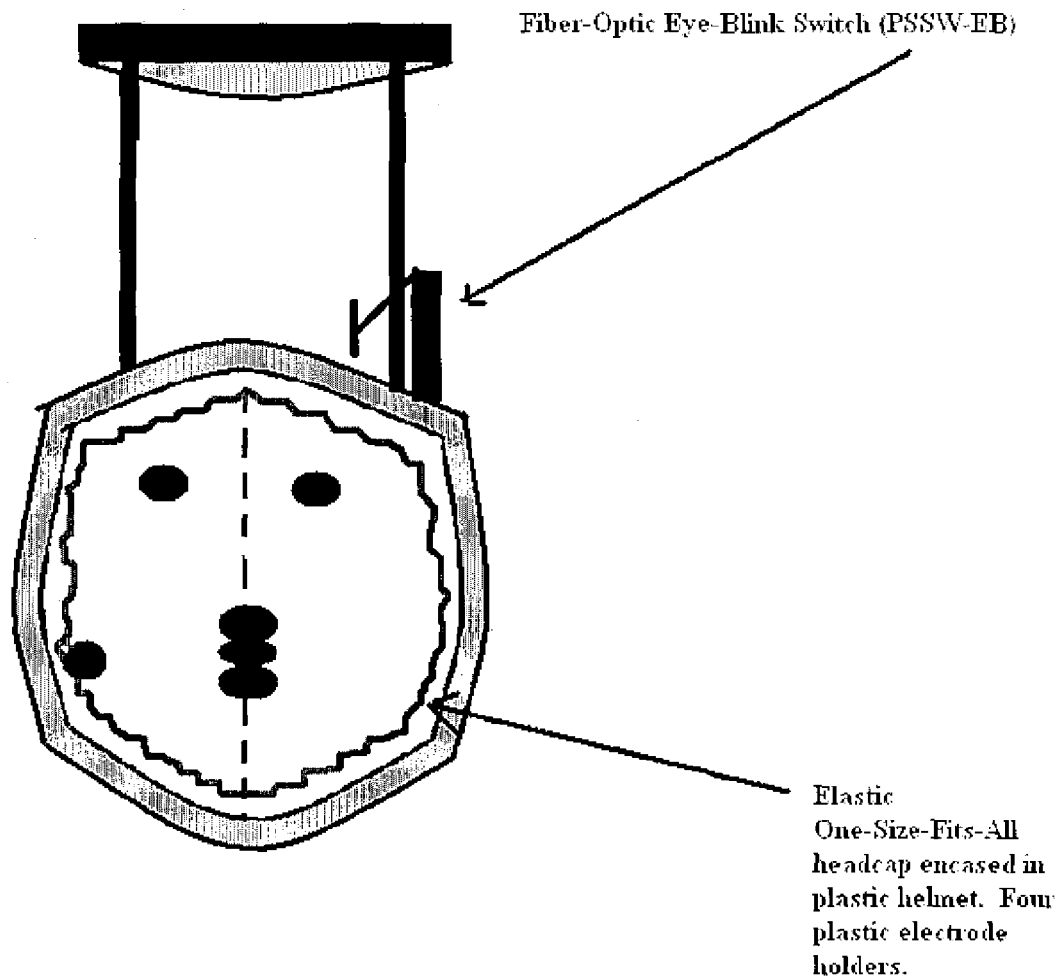
FIG. 4: Top view of Pin electrode EEG headcap device (with fiber optic blink switch)), including an optional screen (e.g. video) for presenting visual images.

The elements that receive and modify the raw EEG signal can be effectively implemented in the current state. The technology that collects the actual EEG signal on the other hand can be modified in order to meet the requirements mentioned above. A design for such device is depicted in FIGS. 3 and 4.

Figure 5:
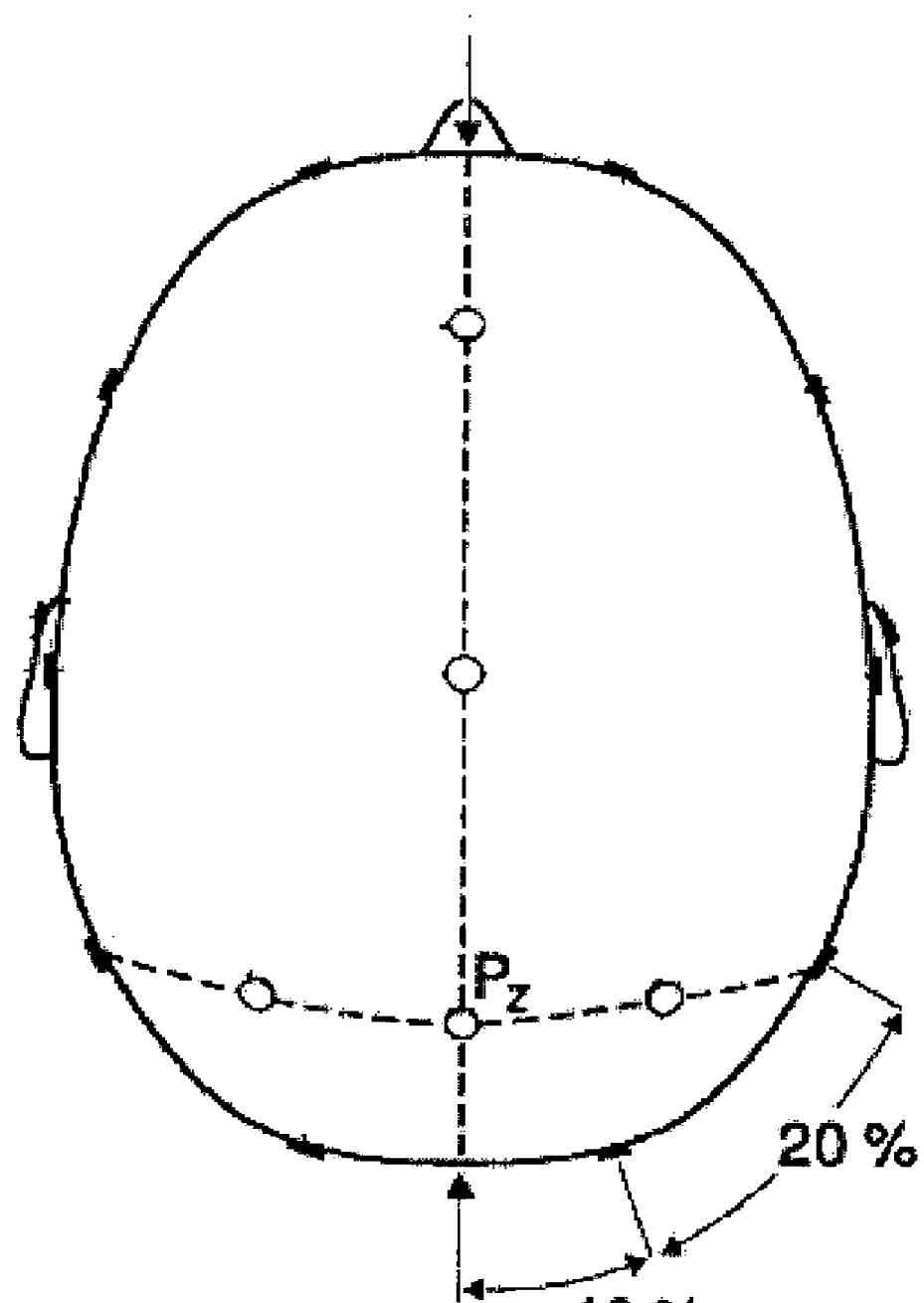
FIG. 5: Pz recording site.

The outside of the device consists of a plastic helmet measuring between 62-66 cm in circumference, able to fit most individuals since head circumferences typically range between 46-62 cm. The helmet has 4 holes for the electrode holders, allowing them to be filled periodically with electrical gel by the person who maintains it. As mentioned above, the use of active electrodes eliminates the need for scalp cleansing and therefore cuts the prep time for EEG recording to significantly nothing. The 3 electrode holders at the top of the helmet are meant for the recording Pz EEG signals. FIG. 5 shows the location of the Pz site on an individual's scalp.

Since typical head circumferences range between 46-62 cm, the 20% mark of the Pz site lies 6.9-9.3 cm from the vertical midline. Therefore, in order to insure that the EEG signal is being recorded from the Pz site of every individual, 3 electrodes are placed 6.9 cm, 8.1 cm and 9.3 cm from the vertical midline of the helmet, respectively. The signals from each electrode are then averaged to produce a single EEG recording. This allows the technology to be used on most individuals without having to worry about different sizes for the device.

The inside of the helmet contains an elastic headcap, similar to the one designed by BioSemi, to which the electrode holders are actually attached. It will comfortably fit on the heads of most individuals and allow for maximal proximity of the electrodes to the scalp. A Fiber Optic Eye Blink Switch attached to the front of the helmet will detect blinks and signal the recording software to eliminate the implicated trials. This eliminates the need for EOG recording and makes the process of gathering data more comfortable for the individual because there are no electrodes or device protrusions touching his face. A video screen can be attached to the front of the helmet to display the appropriate visual stimuli. It can work in conjunction with the EEG recording software and presents stimuli according to the conditions set by the individual running the technology.

EXAMPLES

An individual is attached to an electroencephalograph apparatus for recording (EEG) over a first period of time and it is determined from the EEG that the subject is alert enough to proceed with the testing. Using a bilateral electrode with one pole of the bilateral electrode positioned over the left cerebral hemisphere (LCH) of the test subjects' brain and with another pole of the bilateral electrode positioned over the right cerebral hemisphere (RCH) of the test subjects' brain the individual is exposed during a second period of time to a first series of visual images, the first series comprising at least one image of the face of a second subject and at least four images not of the face of the second subject, and (a) the amplitude of a P300 waveform evoked by the image of the face of the second subject is quantitated and (b) the level of alpha and beta wave activity in the test subject during the second period of time while the EEG is recorded is quantitated. It is determined from the amplitude of the P300 waveform if the second subject is known to the individual. The test subject is then exposed during a third period of time to a second series of visual images which images are predetermined not to evoke a P300 response in a population of test subjects and quantitating the level of alpha and beta wave activity in the test subject during the third period of time so as to determine baseline line alpha and beta wave activity. The baseline alpha and beta wave activity quantitated is subtracted from the alpha and beta wave activity, respectively, so as to produce corrected alpha and beta activity levels. The ratio of corrected alpha wave activity to corrected beta wave activity is then determined, and it is determined if the ratio of corrected alpha wave activity to corrected beta wave activity is higher in the LCH of the test subject or the RCH of the test subject. The individual shows a higher alpha/beta ratio in the LCH indicating that the individual has a sufficiently positive attitude to perform the predefined task with the second subject. Repeating the test with a second individual results in a higher alpha/beta ratio in the RCH indicating that the second individual does not have a sufficiently positive attitude to perform the predefined task with the second subject.

It is determined form a first electroencephalograph (EEG) of a test subject recorded over a first period of time that the test subject is alert enough to proceed with the method. A second EEG is recorded using a bilateral electrode with one pole of the bilateral electrode positioned over the left cerebral hemisphere (LCH) of the test subjects' brain and with another pole of the bilateral electrode positioned over the light cerebral hemisphere (RCH) of the test subjects' brain. The test subject is exposed during a second period of time to a first series of visual images, the first series comprising at least one image of the face of a second subject and at least four images not of the face of the second subject, and (a) the amplitude of a P300 waveform evoked by the image of the face of the second subject is quantitated and (b) the level of alpha and beta wave activity in the test subject during the second period of time is quantitated. It is determined from the amplitude of the P300 waveform if the second subject is known to the test subject. If this is so, a third EEG is recorded over a third period of time from the test subject. The test subject is exposed during the third period of time to a second series of visual images which images are predetermined not to evoke a P300 response in a population of test subjects and the level of alpha and beta wave activity in the test subject during the third period of time is quantitated so as to determine baseline line alpha and beta wave activity. The baseline alpha and beta wave activity is subtracted from the alpha and beta wave activity, respectively, so as to produce corrected alpha and beta activity levels. The ratio of corrected alpha wave activity to corrected beta wave activity is determined and is found to be higher in the LCH of the test subject than the RCH of the test subject. A higher alpha/beta ratio in the RCH than LCH and an alpha/beta ratio in excess of two standard deviations indicates that the subject is content and/or calm. The method is repeated on different test subjects and the following results are found in different individuals: a higher alpha/beta ratio in the LCH than RCH and an alpha/beta ratio in excess of two standard deviations indicating that the subject is sad and/or depressed; a higher alpha/beta ratio in the RCH than LCH and an alpha/beta ratio below two standard deviations indicating that the individual is excited and/or happy; and a higher alpha/beta ratio in the LCH than RCH and an alpha/beta ratio below two standard deviations indicating that the subject is angry and/or afraid.

The examples are repeated wherein the EEG signals are sequentially (a) amplified; (b) filtered through a 30 Hz low pass filter and a 0.3 Hz high pass filter; (c) converted from analog to digital; (d) subjected to a fast Fourier transform and then analyzed to determine the principal components by frequency.

What is claimed is:

1. A method of determining whether a test subject possesses a sufficiently positive attitude to perform a predefined task with a second subject who is known to the test subject comprising:
   a) determining from a first electroencephalograph (EEG) of the test subject recorded over a first period of time if the subject is alert enough to proceed to step b) of the method, and if so, proceeding to step b);
   b) recording a second EEG over a second period of time from the test subject wherein the second EEG is recorded using a bilateral electrode with one pole of the bilateral electrode positioned over the left cerebral hemisphere (LCH) of the test subjects' brain and with another pole of the bilateral electrode positioned over the light cerebral hemisphere (RCH) of the test subjects' brain;
   c) exposing the specific individual during the second period of time to a first series of visual images, the first series comprising at least one image of the face of the second subject and at least four images not of the face of the second subject, and quantitating (a) the amplitude of a P300 waveform evoked by the image of the face of the second subject and (b) the level of alpha and beta wave activity in the test subject during the second period of time;
   d) determining from the amplitude of the P300 waveform if the second subject is known to the test subject;
   e) recording a third EEG over a third period of time from the test subject;
   f) exposing the test subject during the third period of time to a second series of visual images which images are predetermined not to evoke a P300 response in a population of test subjects and quantitating the level of alpha and beta wave activity in the test subject during the third period of time so as to determine baseline line alpha and beta wave activity;
   g) subtracting the baseline alpha and beta wave activity quantitated in step f) from the alpha and beta wave activity, respectively, quantitated in step c) so as to produce corrected alpha and beta activity levels;
   h) determining the ratio of corrected alpha wave activity to corrected beta wave activity,
   i) determining if the ratio of corrected alpha wave activity to corrected beta wave activity is higher in the LCH of the test subject or the RCH of the test subject,
   wherein a higher alpha/beta ratio in the LCH indicates that the test subject has a sufficiently positive attitude to perform the predefined task with the second subject, and wherein a higher alpha/beta ratio in the RCH indicates that the test subject does not have a sufficiently positive attitude to perform the predefined task with the second subject.

2. A method for determining whether a test subject has a mental state in regard to a second subject that is either 1) excited and/or happy; 2) content and/or calm; 3) sad and/or depressed; or 4) angry and/or afraid, the method comprising:
   a) determining from a first electroencephalograph (EEG) of the test subject recorded over a first period of time if the subject is alert enough to proceed to step b) of the method, and if so, proceeding to step b);
   b) recording a second EEG over a second period of time from the test subject wherein the second EEG is recorded using a bilateral electrode with one pole of the bilateral electrode positioned over the left cerebral hemisphere (LCH) of the test subjects' brain and with another pole of the bilateral electrode positioned over the right cerebral hemisphere (RCH) of the test subjects' brain;

c) exposing the specific individual during the second period of time to a first series of visual images, the first series comprising at least one image of the face of the second subject and at least four images not of the face of the second subject, and quantitating (a) the amplitude of a P300 waveform evoked by the image of the face of the second subject and (b) the level of alpha and beta wave activity in the test subject during the second period of time;

d) determining from the amplitude of the P300 waveform if the second subject is known to the test subject;

e) recording a third EEG over a third period of time from the test subject;

f) exposing the test subject during the third period of time to a second series of visual images which images are predetermined not to evoke a P300 response in a population of test subjects and quantitating the level of alpha and beta wave activity in the test subject during the third period of time so as to determine baseline line alpha and beta wave activity;

g) subtracting the baseline alpha and beta wave activity quantitated in step f) from the alpha and beta wave activity, respectively, quantitated in step c) so as to produce corrected alpha and beta activity levels;

h) determining the ratio of corrected alpha wave activity to corrected beta wave activity, i) determining if the ratio of corrected alpha wave activity to corrected beta wave activity is higher in the LCH of the test subject or the RCH of the test subject, wherein (1) a higher alpha/beta ratio in the RCH than LCH and an alpha/beta ratio in excess of two standard deviations indicates that the subject is content and/or calm; (2) a higher alpha/beta ratio in the LCH than RCH and an alpha/beta ratio in excess of two standard deviations indicates that the subject is sad and/or depressed; (3) a higher alpha/beta ratio in the RCH than LCH and an alpha/beta ratio below two standard deviations indicates that the subject is excited and/or happy; and (4) a higher alpha/beta ratio in the LCH than RCH and an alpha/beta ratio below two standard deviations indicates that the subject is angry and/or afraid.

3. The method of claim 1, wherein in step a) the test subject is determined to be alert by i) recording an electroencephalograph (EEG) over a period of time from the test subject using an EEG recording apparatus;

ii) analyzing the frequency distribution of the wavebands recorded in the EEG; and iii) quantitating any ERN waveform in the EEG, wherein presence in the EEG of both (1) (a) an alpha waveband power component ratio of 0.5-1.0 and a theta waveband power component ratio of less than 0.5 or (b) a theta waveband power ratio of 0.5-1.0 and an alpha waveband power component ratio of less than 0.5; and (2) one or more ERN waveforms recorded during the period of time indicates that the test subject is not sufficiently alert to perform the predefined task, and wherein the presence of (1) but not (2), or (2) but not (1), indicates that the test subject is sufficiently alert to perform a predefined task.

4. The method of claim 1, wherein steps e) and f) can be performed before steps b) and c).

5. The method of claim 1 or 2, wherein at least one of the EEGs is recorded using electrodes each comprising an Ag—AgCl recording tip.

6. The method of claim 5, wherein one electrode records from a Pz site on the test subject's head.

7. The method of claim 6, wherein the EEG is recorded using at least Four electrodes, with three recording from the Pz site on the test subject's head and one recording from a mastoid area of the test subject's head.

8. The method of claim 1 or 2, further comprising correcting the first, second and/or third EEG for test subject's eye blinks.

9. The method of claim 8, wherein the EEG is corrected for test subject's eye blinks as measured by a fiber-optic eye blink detector.

10. The method of claim 1 or 2, wherein a 3-D reconstruction of the EEG recorded is not performed.

* * * * *